(12) United States Patent
Barnett et al.

(10) Patent No.: US 8,597,927 B2
(45) Date of Patent: Dec. 3, 2013

(54) ENZYMATIC PREVENTION AND CONTROL OF BIOFILM

(75) Inventors: Christopher C. Barnett, Granite Bay, CA (US); Manoj Kumar, Fremont, CA (US); Gregory M. Whited, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 275 days.

(21) Appl. No.: 12/810,004

(22) PCT Filed: Dec. 16, 2008

(86) PCT No.: PCT/US2008/086959
§ 371 (c)(1),
(2), (4) Date: Jan. 10, 2011

(87) PCT Pub. No.: WO2009/085743
PCT Pub. Date: Jul. 9, 2009

(65) Prior Publication Data
US 2011/0195059 A1  Aug. 11, 2011

Related U.S. Application Data

(60) Provisional application No. 61/015,504, filed on Dec. 20, 2007.

(51) Int. Cl.
*C12N 9/14* (2006.01)
*C12N 9/16* (2006.01)
*C12N 9/18* (2006.01)
*C12N 9/26* (2006.01)
*C12N 9/44* (2006.01)
*C12N 9/48* (2006.01)
*C12N 9/54* (2006.01)
*C12N 9/58* (2006.01)
*C11D 7/42* (2006.01)

(52) U.S. Cl.
USPC ........... 435/195; 435/212; 435/221; 435/223; 435/201; 435/210; 435/196; 435/197; 510/374; 510/218; 510/392

(58) Field of Classification Search
USPC .............................. 424/94.2, 94.6
See application file for complete search history.

(56) References Cited

U.S. PATENT DOCUMENTS

| | | |
|---|---|---|
| RE34,606 E | 5/1994 | Estell et al. |
| 5,310,675 A | 5/1994 | Estell et al. |
| 5,624,829 A | 4/1997 | Sanders et al. |
| 5,736,499 A | 4/1998 | Mitchinson et al. |
| 5,753,484 A | 5/1998 | Ward et al. |
| 5,824,532 A | 10/1998 | Barnett et al. |
| 5,958,739 A | 9/1999 | Mitchinson et al. |
| 7,635,671 B2 * | 12/2009 | Miyazaki et al. ............. 510/320 |
| 2003/0147993 A1 * | 8/2003 | Heddleson et al. ............. 426/42 |
| 2004/0223961 A1 * | 11/2004 | Anderson et al. .......... 424/94.61 |
| 2007/0191248 A1 * | 8/2007 | Souter et al. .................. 510/320 |
| 2008/0233093 A1 * | 9/2008 | McHatton et al. ......... 424/93.46 |

FOREIGN PATENT DOCUMENTS

| | | |
|---|---|---|
| WO | WO 98/26807 | 6/1998 |
| WO | WO 99/14312 | 3/1999 |
| WO | WO 01/53010 | 7/2001 |
| WO | WO 01/98214 | 12/2001 |
| WO | WO 2004/041988 | 5/2004 |
| WO | WO 2005056782 A2 * | 6/2005 |
| WO | WO 2005/124012 | 12/2005 |
| WO | WO 2006/031554 | 3/2006 |
| WO | WO 2008/103747 | 1/2008 |
| WO | WO 2008/051491 | 5/2008 |

OTHER PUBLICATIONS

R. Tallarida., "Drug Synergism and Eose-Effect Data Analysis" Chapman and Hall/CRC Press, 2000, Boca Raton, Chapters 1 and 4 pp. 1-13 and 57-71.*
M Berenbaum, "Synergy, additivism and antagonism in immunosuppression" Clinical Experimental Immunology, 1977, vol. 28 1-18.*
M Berenbaum "What is Synergy?" Pharmacological Reviews, 1989, vol. 41(2) 93-141.*
Altshul et al. (1990) J. Mol. Biol. 215:403-410.
Henikoff et al. (1992) Proc. Natl. Acad. Sci. 89:10915-10919.
Karlin et al. (1993) Proc. Natl. Acad. Sci. 90:5873-5877.
International Search Report dated Feb. 17, 2009.
Higgins et al. (1988) Gene 73:237-244.
Pearson et al. (1988) Proc. Natl. Acad. Sci. 85:2444-2448.
Stahlbrand et al. (1993) J. Biotechnol. 29: 229-242.
Pitts B., et al., J. Microbiological Methods (2003) 54:269-276.

* cited by examiner

Primary Examiner — Blaine Lankford, Jr.
Assistant Examiner — Charles Zoltan Constantine
(74) Attorney, Agent, or Firm — Danisco US Inc.

(57) ABSTRACT

The invention provides methods, compositions, and kits for removal of biofilms from surfaces. The methods described herein comprise simultaneous or sequential application of a perhydrolase enzyme and a mixture of other enzymes, such as proteases, glucanases, esterases, mannanases, phospholipases, cellulases, and/or amylases, to a biofilm on a surface, to effect removal of the biofilm.

5 Claims, No Drawings

SEQUENCE LISTING

<160> NUMBER OF SEQ ID NOS: 2

<210> SEQ ID NO 1
<211> LENGTH: 216
<212> TYPE: PRT
<213> ORGANISM: Mycobacterium smegmatis

<400> SEQUENCE: 1

```
Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175
```

```
Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215

<210> SEQ ID NO 2
<211> LENGTH: 651
<212> TYPE: DNA
<213> ORGANISM: Mycobacterium smegmatis

<400> SEQUENCE: 2
atggccaagc gaattctgtg tttcggtgat tccctgacct ggggctgggt ccccgtcgaa      60
gacggggcac ccaccgagcg gttcgccccc gacgtgcgct ggaccggtgt gctggcccag     120
cagctcggag cggacttcga ggtgatcgag gagggactga gcgcgcgcac caccaacatc     180
gacgacccca ccgatccgcg gctcaacggc gcgagctacc tgccgtcgtg cctcgcgacg     240
cacctgccgc tcgacctggt gatcatcatg ctgggcacca acgacaccaa ggcctacttc     300
cggcgcaccc cgctcgacat cgcgctgggc atgtcggtgc tcgtcacgca ggtgctcacc     360
agcgcgggcg gcgtcggcac cacgtacccg gcacccaagg tgctggtggt ctcgccgcca     420
ccgctggcgc ccatgccgca cccctggttc cagttgatct tcgagggcgg cgagcagaag     480
accactgagc tcgcccgcgt gtacagcgcg ctcgcgtcgt tcatgaaggt gccgttcttc     540
gacgcgggtt cggtgatcag caccgacggc gtcgacggaa tccacttcac cgaggccaac     600
aatcgcgatc tcggggtggc cctcgcggaa caggtgcgga gcctgctgta a               651
```

ENZYMATIC PREVENTION AND CONTROL OF BIOFILM

CROSS-REFERENCE TO RELATED APPLICATIONS

This application claims the benefit of U.S. provisional application No. 61/015,504, filed on Dec. 20, 2007, which is incorporated by reference herein in its entirety.

FIELD OF THE INVENTION

The invention relates to enzyme compositions and methods for removal of biofilms from surfaces. In particular, methods for biofilm removal include application of a perhydrolase enzyme in combination with other enzymes to a biofilm on a surface.

BACKGROUND

Biofilms consist of an attached community of microorganisms embedded in a slimy exopolymer matrix that often persists despite control attempts with traditional approaches designed to kill free-floating microorganisms. The resistance of biofilms to antibiotics, antiseptics, and oxidizing biocides has been well documented.

Enzymatic methods for biofilm prevention and/or reduction have been described, for example, in PCT Application Nos. WO 06/031554, WO 01/98214, WO 98/26807, WO 04/041988, WO 99/14312, and WO 01/53010. However, there is a need for improved methods and compositions for control of biofilms in industrial, dental, and health care applications.

BRIEF SUMMARY OF THE INVENTION

The invention provides methods, compositions, and kits for biofilm removal. In one aspect, the invention provides a method for removing biofilm from a surface, said method comprising applying a perhydrolase enzyme and a removal enzyme mixture to said biofilm for a time sufficient to reduce said biofilm by at least 25%, wherein said enzyme mixture is selected from protease, glucanase, and esterase; protease, glucanase, esterase, and mannanase; protease, glucanase, phospholipase, and mannanase; three proteases, glucanase, phospholipase, and mannanase; three proteases, glucanase, and mannanase; two proteases, cellulase, glucanases, phospholipase, and mannanase; protease, glucanase, and mannanase; protease, cellulase, phospholipase, and esterase; two proteases, glucanase, phospholipase, and esterase; two proteases, glucanase, phospholipase, and mannanase; three proteases, cellulase, phospholipase, and glucanase; three proteases, cellulase, phospholipase, and mannanase; three proteases, glucanase, phospholipase and esterase; protease, cellulase, glucanase, phospholipase, and esterase; at least two amylases and glucanase; at least three amylases; and at least two amylases, glucanase, and protease. In some embodiments, the biofilm comprises *Pseudomonas aeruginosa*, *Listeria monocytogenes*, or *Staphylococcus aureus*. In some embodiments, the perhydrolase enzyme comprises the amino acid sequence set forth in SEQ ID NO:1 or a variant or homologue thereof. In one embodiment, the perhydrolase enzyme is the S54V variant of SEQ ID NO:1.

In one embodiment, the removal enzyme mixture consists of three proteases, glucanase, phospholipase, and mannanase. In one embodiment, the removal enzyme mixture consists of PROPERASE, PURAFECT, FNA, LAMINEX BG, GC 265, and LYSOMAX.

In one embodiment, the perhydrolase enzyme and the removal enzyme mixture are applied to the biofilm simultaneously. In another embodiment, the perhydrolase enzyme mixture and the removal enzyme mixture are applied to the biofilm sequentially. In one embodiment, the perhydrolase enzyme is applied prior to application of the removal enzyme mixture. In one embodiment, the perhydrolase enzyme and the removal enzyme mixture act synergistically to remove the biofilm from the surface.

In another aspect, the invention provides a composition for removing biofilm from a surface, said composition comprising a perhydrolase enzyme and a removal enzyme mixture, wherein said removal enzyme mixture is selected from protease, glucanase, and esterase; protease, glucanase, esterase, and mannanase; protease, glucanase, phospholipase, and mannanase; three proteases, glucanase, phospholipase, and mannanase; three proteases, glucanase, and mannanase; two proteases, cellulase, glucanases, phospholipase, and mannanase; protease, glucanase, and mannanase; protease, cellulase, phospholipase, and esterase; two proteases, glucanase, phospholipase, and esterase; two proteases, glucanase, phospholipase, and mannanase; three proteases, cellulase, phospholipase, and glucanase; three proteases, cellulase, phospholipase, and mannanase; three proteases, glucanase, phospholipase and esterase; protease, cellulase, glucanase, phospholipase, and esterase; at least two amylases and glucanase; at least three amylases; and at least two amylases, glucanase, and protease.

In one embodiment, the removal enzyme mixture consists of three proteases, glucanase, phospholipase, and mannanase. In one embodiment, the removal enzyme mixture consists of PROPERASE, PURAFECT, FNA, LAMINEX BG, GC 265, and LYSOMAX.

In some embodiments, the perhydrolase enzyme comprises the amino acid sequence set forth in SEQ ID NO:1 or a variant or homologue thereof. In one embodiment, the perhydrolase enzyme is the S54V variant of SEQ ID NO:1.

In another aspect, the invention provides a kit for removing biofilm from a surface, said kit comprising a perhydrolase enzyme and a removal enzyme mixture, wherein said enzyme mixture is selected from the group consisting of protease, glucanase, and esterase; protease, glucanase, esterase, and mannanase; protease, glucanase, phospholipase, and mannanase; three proteases, glucanase, phospholipase, and mannanase; three proteases, glucanase, and mannanase; two proteases, cellulase, glucanases, phospholipase, and mannanase; protease, glucanase, and mannanase; protease, cellulase, phospholipase, and esterase; two proteases, glucanase, phospholipase, and esterase; two proteases, glucanase, phospholipase, and mannanase; three proteases, cellulase, phospholipase, and glucanase; three proteases, cellulase, phospholipase, and mannanase; three proteases, glucanase, phospholipase and esterase; protease, cellulase, glucanase, phospholipase, and esterase; at least two amylases and glucanase; at least three amylases; and at least two amylases, glucanase, and protease, and optionally, instructions for use in a method for removal of a biofilm as described herein. In one embodiment, the perhydrolase enzyme removal enzyme mixture are in separate containers. In one embodiment, the perhydrolase enzyme and the removal enzyme mixture are in the same container.

In one embodiment, the removal enzyme mixture consists of three proteases, glucanase, phospholipase, and mannanase.

In one embodiment, the removal enzyme mixture consists of PROPERASE, PURAFECT, FNA, LAMINEX BG, GC 265, and LYSOMAX.

In some embodiments, the perhydrolase enzyme comprises the amino acid sequence set forth in SEQ ID NO:1 or a variant or homologue thereof In one embodiment, the perhydrolase enzyme is the S54V variant of SEQ ID NO:1.

DETAILED DESCRIPTION

The invention provides methods, compositions, and kits for control, i.e., elimination or reduction, of a biofilm on a surface or prevention of formation or growth of a biofilm on a surface. Enzyme-containing compositions and methods of the invention are applicable to control of biofilms in, for example, industrial water management such as cooling towers, drinking water, waste water, dental hygiene, medical implants and devices, hemodialysis systems, oil recovery, bioremediation wells, paper and pulp processing, ship hulls, food processing equipment, and water delivery systems, e.g., pipes, tubing, and the like.

Unless defined otherwise herein, all technical and scientific terms used herein have the same meaning as commonly understood by one of ordinary skill in the art. Singleton, et al., *Dictionary of Microbiology and Molecular Biology*, second ed., John is Wiley and Sons, New York (1994), and Hale & Markham, *The Harper Collins Dictionary of Biology*, Harper Perennial, N.Y. (1991) provide one of skill with a general dictionary of many of the terms used in this invention. Any methods and materials similar or equivalent to those described herein can be used in the practice or testing of the present invention.

Numeric ranges provided herein are inclusive of the numbers defining the range.

Unless otherwise indicated, nucleic acids are written left to right in 5' to 3's orientation; amino acid sequences are written left to right in amino to carboxy orientation, respectively.

DEFINITIONS

A "biofilm" refers to a community of microorganisms embedded in an extracellular polymer matrix attached to a surface. A biofilm further includes water and may include other trapped particles. A biofilm may include one or more microorganisms, including gram-positive or gram-negative bacteria (aerobic or anaerobic), algae, protozoa, and/or yeast or filamentous fungi. In some embodiments, the biofilm includes living cells of bacterial genera of *Staphylococcus, Streptomyces, Pseudomonas, Listeria, Streptococcus*, and *Escherichia*.

A "surface" refers to any structure having sufficient mass to allow for attachment of a biofilm. Hard surfaces include, but are not limited to, metal, glass, ceramic, wood, mineral (e.g., rock, stone, marble, granite), aggregate materials such as concrete, plastic, composite material, hard rubber material, and gypsum. A hard material may be finished with enamel and/or paint. Hard surfaces are found, for example, in water treatment and storage equipment and tanks, dairy and food processing equipment and facilities, medical equipment and facilities, e.g., surgical instruments, permanent and temporary implants, and industrial pharmaceutical equipment and plants. Soft surfaces include, but are not limited to, hair and textiles. Porous surfaces may be biological surfaces, including, but not limited to, skin, keratin, and internal organs. Porous surfaces may also be found in certain ceramics as well as in membranes that are used for filtration. Other surfaces include, but are not limited to, ship hulls and swimming pools.

"Enzyme dosage" refers to an amount of an enzyme mixture, an amount of a single enzyme in an enzyme mixture, or an amount of a single enzyme used alone, utilized to treat a biofilm. Factors affecting enzyme dosage include, but are not limited to, the type of enzyme, the surface to be treated, and the intended result. In some embodiments, the enzyme dosage is the amount of enzyme mixture needed to reduce biofilm by at least about 20, 25, 30, 35, 40, 45, 50, 55, 60, 65, 70, 75, 80, 85, 90, 95, 98, or 99%. In general, the enzyme content in an enzyme mixture is in total about 1% or less, 2% or less, 3% or less, or 5% or less (w/w).

"Treatment" or "control" or "removal" of a biofilm refers to reduction or elimination of biofilm from a surface, including killing and/or inhibition of growth of microbes in the biofilm, and/or prophylactic prevention of formation of or growth of a biofilm on a surface.

An "enzyme mixture" refers to at least two enzymes. Enzymes used in enzyme mixtures described herein may be derived from plant or animal sources, bacteria, fungi, or yeast, and may be wild type or variant enzymes.

"Acid conditions," "neutral conditions," and "basic conditions" are well known to those skilled in the art. Typically, "acid conditions" refers to a pH of about 4 to about 6. "Neutral conditions" refers to a pH of about 6 to about 8. "Basic conditions" refers to a pH of about 8 to about 10.

A "perhydrolase" refers to an enzyme that is capable of catalyzing a perhydrolysis reaction that results in the production of a sufficiently high amount of peracid suitable for use in an application such as cleaning, bleaching, disinfection, or sterilization of an object (e.g., treatment of a biofilm as described herein). Generally, a perhydrolase enzyme used in methods described herein exhibits a high perhydrolysis to hydrolysis ratio. In some embodiments, the perhydrolase comprises, consists of, or consists essentially of the *Mycobacterium smegmatis* perhydrolase amino acid sequence set forth in SEQ ID NO:1, or a variant or homolog thereof. In some embodiments, the perhydrolase enzyme comprises acyl transferase activity and catalyzes an aqueous acyl transfer reaction.

A "peracid" is an organic acid of the formula $RC(=O)OOH$.

"Perhydrolysis" or "perhydrolyze" refers to an enzymatic reaction that produces a peracid. In some embodiments, a peracid is produced by perhydrolysis of an ester substrate of the formula $R_1C(=O)OR_2$, where $R_1$ and $R_2$ are the same or different organic moieties, in the presence of hydrogen peroxide ($H_2O_2$).

The phrase "source of hydrogen peroxide" includes hydrogen peroxide as well as the components of a system that can spontaneously or enzymatically produce hydrogen peroxide as a reaction product.

The phrase "perhydrolysis to hydrolysis ratio" refers to the ratio of the amount of enzymatically produced peracid to the amount of enzymatically produced acid by a perhydrolase enzyme from an ester substrate under defined conditions and within a defined time.

As used herein, the term "acyl" refers to an organic acid group, which is the residue of a carboxylic acid after removal of a hydroxyl (—OH) group (e.g., ethanoyl chloride, $CH_3CO$—Cl, is the acyl chloride formed from ethanoic acid, $CH_3CO$-OH). The name of an individual acyl group is general formed by replacing the "-ic" of the acid by "-yl."

As used herein, the term "acylation" refers to a chemical transformation in which an acyl (RCO—) group is substituted into a molecule, generally for an active hydrogen of an —OH group.

As used herein, the term "transferase" refers to an enzyme that catalyzes the transfer of a functional group from one substrate to another substrate.

As used herein, "protein" refers to any composition comprised of amino acids and recognized as a protein by those of skill in the art. The terms "polypeptide," "oligopeptide," "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "multimer" refers to two or more proteins or peptides that are covalently or non-covalently associated and exist as a complex in solution. A "dimer" is a multimer that contains two proteins or peptides; a "trimer" contains three proteins or peptides, etc. As used herein, "octamer" refers to a multimer of eight proteins or peptides. The proteins or peptides of a multimer may be the same or different.

As used herein, "effective amount of an enzyme" refers to the quantity of enzyme necessary to achieve the enzymatic activity required in a specific application (e.g., removal of a biofilm).

As used herein, functionally and/or structurally similar proteins are considered to be "related proteins." In some embodiments, related proteins are derived from a different genus and/or species, including differences between classes or organisms (e.g., a bacterial protein and a fungal protein). In some embodiments, related proteins are derived from the same species. In addition, the term "related proteins" encompasses tertiary structural homologs and primary sequence homologs. The term also encompasses proteins that are immunologically cross-reactive. In some embodiments, related perhydrolase enzymes exhibit high ratios of perhydrolysis to hydrolysis.

As used herein, the term "derivative" refers to a protein which is derived from a parent protein by addition of one or more amino acids to either or both of the C- and N-terminal end(s), substitution of one or more amino acids at one or a number of different sites in the amino acid sequence, and/or deletion of one or more amino acids at either or both C- and N-terminal end(s) and/or at one or more sites in the amino acid sequence, and/or insertion of one or more amino acids at one or more sites in the amino acid sequence. The preparation of a protein derivative is often achieved by modifying a DNA sequence that encodes a native protein, transformation of the modified DNA sequence into a suitable host, and expression of the modified DNA sequence to produce the derivative protein.

Related (and derivative) proteins encompass "variant" proteins. Variant proteins differ from a parent protein and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids.

In some embodiments, related proteins, such as variant proteins, comprise any of at least about 35%, 40%, 45%, 50%, 55%, 60%, 65%, 70%, 75%, 80%, 85%, 90%, 95%, 97%, 98%, 99%, or 99.5% amino acid sequence identity.

As used herein, the term "analogous sequence" refers to a polypeptide sequence within a protein that provides a similar function, tertiary structure, and/or conserved residues with respect to a reference protein. For example, in epitope regions that contain an alpha helix or a beta sheet structure, replacement amino acid(s) in an analogous sequence maintain the same structural element. In some embodiments, analogous sequences are provided that result in a variant enzyme exhibiting a similar or improved function with respect to the parent protein from which the variant is derived.

As used herein, "homologous protein" refers to a protein (e.g., a perhydrolase enzyme) that has similar function (e.g., enzymatic activity) and/or structure as a reference protein (e.g., a perhydrolase enzyme from a different source). Homologs may be from evolutionarily related or unrelated species. In some embodiments, a homolog has a quaternary, tertiary and/or primary structure similar to that of a reference protein, thereby potentially allowing for replacement of a segment or fragment in the reference protein with an analogous segment or fragment from the homolog, with reduced disruptiveness of structure and/or function of the reference protein in comparison with replacement of the segment or fragment with a sequence from a non-homologous protein.

As used herein, "corresponding to" refers to an amino acid residue in one protein or peptide that is analogous, homologous, or equivalent to an enumerated amino acid residue in another protein or peptide.

As used herein, "corresponding region" refers to an analogous, homologous, or equivalent positions or region in the polypeptide sequences of two proteins or peptides, including two derivative or variant proteins or a derivative or variant protein and a parent protein.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The phrases "substantially similar" and "substantially identical" in the context of at least two nucleic acids or polypeptides typically means that a polynucleotide or polypeptide comprises a sequence that has at least about 40%, 45%, 50%, 55%, 60%, 65%, 70%, 75%, 80%, 85%, 90%, 95%, 97%, 98%, 99%, or 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) *J. Mol. Biol.* 215:403-410; Henikoff et al. (1989) *Proc. Natl. Acad. Sci.* 89:10915; Karin et al. (1993) *Proc. Natl. Acad. Sci.* 90:5873; and Higgins et al. (1988) Gene 73:237). Software for performing BLAST analyses is publicly available through the National Center for Biotechnology Information. Also, databases may be searched using FASTA (Person et al. (1988) *Proc. Natl. Acad. Sci.* 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

An "isolated" polypeptide or polynucleotide is one that is substantially free of the materials with which it is associated in nature. By substantially free is meant at least 50%, often at least 70%, more often at least 80%, and even more often at least 90% free of the materials with which it is associated in nature.

Enzyme Mixtures

A number of different enzymes may be used in the enzyme mixtures and methods described herein for biofilm reduction. Enzyme mixtures described herein include at least two enzymes, such as combinations of carbohydrases, such as cellulases, endoglucanases, cellobiohydrolases, and beta-glucosidases; amylases, such as alpha-amylases; proteases, such as serine proteases, e.g., subtilisins; esterases and cutinases; granular starch hydrolyzing enzymes; lipases, such as phospholipases; and hemicellulases, such as mannanases. Such an enzyme mixtures is also termed a "removal enzyme mixture" herein, and includes a combination of enzymes as described herein. A removal enzyme mixture does not include a perhydrolase enzyme, but is used in combination with one or more perhydrolase enzymes, either concurrently or sequentially, in a method for biofilm reduction as described herein.

Hydrolases (E.C.3.) that may be used include, for example, proteases, glucanases (family 16 glycosyl hydrolase), cellulases, esterases, mannanases, and arabinases. Neutral and serine proteases, e.g., subtilisins, may be used for the present invention. Neutral proteases are proteases that have optimal proteolytic activity in the neutral pH range of approximately 6 to 8. Suitable neutral proteases are aspartate and metallo proteases. Commercially suitable metallo-proteases are MULTIFECT, PURAFECT L, FNA, PROPERASE L, PURADAX EG7000L, and GC106 from *Aspergillus niger*, all available from Genencor Division, Danisco US, Inc., Palo Alto ("Genencor"), Calif., and Alcalase, Savinase, Esperase and Neutrase (Novo Nordisk A/S, Denmark). The neutral proteases may be derived from bacterial, fungal or yeast sources, or plant or animal sources and may be wild type or variant enzymes. Variant enzymes are produced in sources that express genes that were mutated from parent genes.

Examples of cellulases that may be used for the present invention include endoglucanases, cellobiohydrolases and beta-glucosidases, including cellulases having optimal activity in the acid to neutral pH range, for example, PURADAX derived from a bacterial source, or LAMINEX and INDIAGE from Genencor, both derived from a fungal source. Cellulases may be derived, for example, from fungi of the genera *Aspergillus, Trichoderma, Humicola, Fusarium*, and *Penicillium*.

Examples of useful granular starch hydrolyzing enzymes include glucoamylases derived from strains of *Humicola, Aspergillus*, and *Phizopus*. Granular starch hydrolyzing (GSH) enzymes refers to enzymes that hydrolyze starch in granular form. Glucoamylase refers to the amyloglucosidase class of enzymes (e.g., EC.3.2.1.3 glucoamylase, 1,4-alpha-D-glucan glucohydrolase.). These are exo-acting enzymes that release glucosyl residues from the non-reducing ends of amylose and amylopectin molecules. The enzyme also hydrolyzes alpha-1, 6 and alpha-1,3 linkages. Glucoamylase activity may be measured using the well-known assay based on the ability of glucoamylase to catalyze the hydrolysis of p-nitrophenyl-alpha-D-glucopyranoside (PNPG) to glucose and p-nitrophenol. At an alkaline pH, the nitrophenol forms a yellow color that is proportional to glucoamylase activity and is monitored at 400 nm prior to comparison against an enzyme standard measured as a GAU. A GAU (glucoamylase activity unit) is defined as the amount of enzyme that will produce 1 gm of reducing sugar, calculated as glucose per hour from a soluble starch substrate (4% ds) at pH 4.2 and 60° C. Suitable commercially available glucoamylases from Genencor include OPTIDEX, DISTILLASE, and G-ZYME.

Examples of lipases that may be used for the present invention include acid, neutral and alkaline lipases and phospholipases. Commercially available lipases and phospholipases from Genencor include LYSOMAX and CUTINASE.

Examples of hemicellulase mannanases that may be used for the present invention include GC265 from *Bacillus lentus*, HEMICELL and PURABRITE, both from *Bacillus lentus*, from Genencor, and the mannanases described in Stahlbrand et al. (1993) *J. Biotechnol.* 29: 229-242.

Examples of esterases and cutinases that may be used for the present invention may be from any source, including, for example bacterial sources such as *Pseudomonas mendocina* or fungal sources such as *Humicula* or *Fusarium*. Several of such enzymes are available from Genencor.

Examples of amylases that may be used in the present invention include alpha or beta amylases which may be obtained from bacterial or fungal sources, such as Bacillus amylases (*B. amyloliquefaciens, B. licheniformis*, and *B. stearothermophilus*) and fungal amylases, for example, from *Aspergillus*, e.g. *A. niger, A. kawachi*, or *A. oryzae, Humicola*, and *Trichoderma*. Amylases available from Genencor include SPEZYME FRED, SPEZYME AA, CLARASE, AMYLEX and the mixture of amylases SPEZYME ETHYL. Amylases available from Novozymes A/S (Denmark) include BAN, AQUAZYM, AQUAZYM Ultra, and TERMAMYL. Other amylases include mixtures of amylases, such as M1 from Biocon, and CuConc from Sumizyme, Aris Sumizyme L (endo 1,5 alpha-L arabinase), ACH Sumizyme (beta mannase), *Humicola* glucoamylase, dextranase, dextramase, chitinase, ENDOH, and OPTIMAX L1000 (glucoamylase).

As described in co-pending PCT application no. PCT/US2007/016461, over 375 different enzyme mixtures were tested for biofilm removal properties. The screening resulted in the identification of 33 surprising enzyme mixtures that resulted in substantial biofilm reduction. The 33 enzyme mixtures include mixtures of an alpha amylase and a mannanase; an amylase and a protease; an amylase and arabinase; at least one alpha amylase and at least two other amylases; a protease, cellulase and glucanase; a protease, cellulase, and three glucanases; a protease, cellulase and mannanase; a protease, cellulase and amylase; a protease, amylase, and glucanase; a protease, mannanase, and amylase; a cellulase, arabinase and amylase; a protease, cellulase, mannanase and phopholipase; a protease, glucanase, amylase, and arabinase; a protease, cellulase, and two glucanases; a protease, cellulase, and three glucanases; three proteases, a cellulase, a mannanase, and a phospholipase; three proteases, cellulase, phospholipase and esterase; three proteases, a mannanase, phospholipase and esterase; three proteases, a cellulase, and a mannanase; two proteases, cellulase, and glucanase; two proteases, cellulase, glucanase, and mannanase; two proteases, a cellulase, glucanases, phospholipase and mannanase; at least three amylases and a cellulase; an amylase, arabinase, and cellulase; an amylase, arabinase and protease; at least three amylases and a protease; at least three amylases, a protease, and a cellulase; a glucanase and an amylase mixture; a cellulase and an amylase mixture.

In some embodiments, one of the following enzyme mixtures is used: protease, glucanase and esterase; protease glucanase, esterase and mannanase; protease, glucanase, phospholipase and mannanase; three proteases, glucanase, phospholipase and mannanase; three proteases, phospholipase, esterase and mannanase; three proteases, glucanase and mannanase; two proteases, cellulase, glucanase, phospholipase and mannanase; protease, glucanase and mannanase; protease, cellulase, phospholipase and esterase; two proteases, glucanase, phospholipase and esterase; two proteases, glucanase, phospholipase and mannanase; three proteases, cellulase, phospholipase and glucanase; three proteases, cellulase, phospholipase and mannanase; three proteases, glucanase, phospholipase and esterase; protease, cellulase, glucanase, phospholipase and esterase; two or more amylases and glucanase; at least three amylases; at least two amylases, glucanase and protease.

In some embodiments, one of the following enzyme mixtures is used: protease, glucanase and cutinase, which may be prepared using the commercially availably enzymes MULTIFECT NEUTRAL; LAMINEX BG and cutinase; protease, glucanase, mannanase and cutinase, which may be prepared using the commercially availably enzymes MULTIFECT NEUTRAL; LAMINEX BG; mannanase and cutinase; protease, glucanase, mannanase and phospholipase, which may be prepared using the commercially available enzymes MULTIFECT NEUTRAL; LAMINEX BG; mannanase and LYSOMAX; a mixture of three proteases plus cellulase, mannanase, and cutinase, which may be prepared using the commercially availably enzymes PROPERASE L; PURAFECT L; FNA; and LAMINEX BG, mannanase and cutinase.

Some embodiments of the present invention include the following commercially available enzyme preparations from Genencor: MULTIFECT NEUTRAL; LAMINEX; LYSOMAX; PROPERASE; PURADAX, PURAFECT; and SPEZYME, all of which are registered trademarks of Genencor.

MULTIFECT NEUTRAL comprises a *Bacillus amyloliquefaciens* protease (EC3.4.24.28); LAMINEX BG, having an activity level or about 3200 IU/g, comprises a *Trichoderma B*-glucanase (cellulase EC3.3.1.6); LYSOMAX, having an activity level of about 400 U/g, comprises a *Streptomyces violceoruber* phospholipase; PROPERASE having an activity level of about 1600 PU/g, comprises a *Bacillus alcalophilus* protease (EC3.4.21.62); PURAFECT, having an activity of about 42,000 GSU/g, comprises a subtilisin protease (EC3.4.21.62), as described in U.S. Pat. No. 5,624,829; FNA comprises a *Bacillus subtilis* protease (EC3.4.21.62), as described in U.S. Pat. Nos. RE 34,606 and 5,310,675; PURADAX, having an activity level of about 32 U/g, comprises *Trichoderma reesei* cellulase (EC3.2.1.4), as described in U.S. Pat. No. 5,753,484; SPEZYME FRED, having an activity level of about 15,100 LU/g, comprises an alpha amylase from *Bacillus licheniformis* (EC3.2.1.1), as described in U.S. Pat. Nos. 5,736,499; 5,958,739; and 5,824,532.

In some embodiments, enzyme mixtures using commercially available enzyme include the following:

1. MULTIFECT NEUTRAL; LAMINEX BG and cutinase.
2. MULTIFECT NEUTRAL; LAMINEX BG; mannanase and cutinase.
3. MULTIFECT NEUTRAL; LAMINEX BG; mannanase and LYSOMAX.
4. PROPERASE L; PURAFECT L; FNA; LAMINEX BG, mannanase and cutinase.
5. PROPERASE L; PURAFECT L; FNA; mannanase, cutinase and LYSOMAX.
6. PROPERATE L; PURAFECT L, FNA, mannanase, LAMINEX BG.
7. MULTIFECT NEUTRAL; LAMINEX BG; and mannanase.
8. FNA; PURADAX EG 7000L; LAMINEX BG, and cutinase.
9. PURAFECT L; FNA; LAMINEX BG; and LYSOMAX.
10. PROPERASE L; FNA; LAMINEX BG; and LYSOMAX.
11. PROPERASE L; PURAFECT L; FNA; LAMINEX BG; PURADAX EG 7000L; and LYSOMAX.
12. PROPERASE L; PURAFECT L; FNA; LAMINEX BG; cutinase and LYSOMAX.
13. MULTIFECT NEUTRAL; PURADAX EG 7000L; LAMINEX BG; LYSOMAX; and cutinase.
14. PROPERASE L; LAMINEX BG; LYSOMAX and cutinase.

In some embodiments, enzyme mixtures are the combinations 1, 2, 3 and 4 listed above. Additional enzyme combinations include: SPEZYME, which comprises an alpha amylase obtained from *Bacillus licheniformis*; CuCONC, which is the trade name for the Koji strain of *Rhizopus niveus* glucoamylase, which has granular starch hydrolyzing activity (Shin Nihon Chemical Co. Ltd. Japan); AFP GC 106, which is an acid fungal protease (Shin Hihon Chemical Co. Ltd. Japan); M1, which is available from Biocon India, Ltd., Bangalore, India); ARIS SUMIZYME (1,5-alpha arabinase); and ACH SUMIZYME.

15. SPEZYME FRED L; CuCON and LAMINEX BG.
16. SPEZYME FLRED L; Aris SUMIZYME and LAMINEX BG.
17. SPEZYME FRED L and CuCONC.
18. SPEZYME FRED L; CuCONC and GC106.
19. SPEZYME FRED L and GC106.
20. SPEZYME FRED L and M1.
21. SPEZYME FRED L; Aris SUMIZYME and GC106.
22. SPEZYME FRED L; CuCONC; LAMINEX BG and GC106.
23. SPEZYME FRED L; ACH SUMIZYME and GC106.
24. SPEZYME FRED L; Aris SUMIZYME; LAMINEX BG and GC106.
25. CuCONC and LAMINEX BG.
26. SPEZYME FRED L and Aris SUMIZYME.
27. M1 and LAMINEX BG.
28. SPEZYME FRED L; LAMINEX BG and GC106.
29. CuCONC; LAMINEX BG and GC106.

Perhydrolase Enzyme

One or more perhydrolase enzymes may be used in methods of the invention for biofilm removal, in conjunction with enzyme mixtures as described above.

In some embodiments, a perhydrolase enzyme is naturally-occurring (i.e., a perhydrolase enzyme encoded by a genome of a cell). In some embodiments, a perhydrolase enzyme comprises, consists of, or consists essentially of an amino acid sequence that is at least about 80%, 85%, 90%, 95%, 97%, 98%, 99%, or 99.5% identical to the amino acid sequence of a naturally-occurring perhydrolase enzyme.

In some embodiments, a perhydrolase enzyme is a naturally occurring *M. smegmatis* perhydrolase enzyme. In some embodiments, a perhydrolase enzyme comprises, consists of, or consists essentially of the amino acid sequence set forth in SEQ ID NO:1 or a variant or homologue thereof. In some embodiments, a perhydrolase enzyme comprises, consists of, or consists essentially of an amino acid sequence that is at least about 80%, 85%, 90%, 95%, 97%, 98%, 99%, or 99.5% identical to the amino acid sequence set forth in SEQ ID NO:1.

The amino acid sequence of *M. smegmatis* perhydrolase is shown below: MAKRILCFGDSLTWGWVP-VEDGAPTERFAPDVRWTGVLAQQLGADFEVIEEGL SARTTNIDDPTDPRLNGASYLPSCLATH-LPLDLVIIMLGTNDTKAYFRRTPLDIAL GMSVLVTQV-LTSAGGVGTTYPAPKVLVVSPPPLAP- MPHPWFQLIFEGGEQKTTE
LARVYSALASFMKVPFFDAGS-
VISTDGVDGIHFTEANNRDLGVALAEQVRSLL (SEQ ID NO:1)

The corresponding polynucleotide sequence encoding *M. smegmatis* perhydrolase is:

(SEQ ID NO: 2)

5'-

ATGGCCAAGCGAATTCTGTGTTTCGGTGATTCCCTGACCTGGGGCTGGGT

CCCCGTCGAAGACGGGGCACCCACCGAGCGGTTCGCCCCGACGTGCGCT

GGACCGGTGTGCTGGCCCAGCAGCTCGGAGCGGACTTCGAGGTGATCGAG

GAGGGACTGAGCGCGCGCACCACCAACATCGACGACCCCACCGATCCGCG

GCTCAACGGCGCGAGCTACCTGCCGTCGTGCCTCGCGACGCACCTGCCGC

TCGACCTGGTGATCATCATGCTGGGCACCAACGACACCAAGGCCTACTTC

CGGCGCACCCCGCTCGACATCGCGCTGGGCATGTCGGTGCTCGTCACGCA

GGTGCTCACCAGCGCGGGCGGCGTCGGCACCACGTACCCGGCACCCAAGG

TGCTGGTGGTCTCGCCGCCACCGCTGGCGCCCATGCCGCACCCCTGGTTC

CAGTTGATCTTCGAGGGCGGCGAGCAGAAGACCACTGAGCTCGCCCGCGT

GTACAGCGCGCTCGCGTCGTTCATGAAGGTGCCGTTCTTCGACGCGGGTT

CGGTGATCAGCACCGACGGCGTCGACGGAATCCACTTCACCGAGGCCAAC

AATCGCGATCTCGGGGTGGCCCTCGCGGAACAGGTGCGGAGCCTGCTGTA

A-3'

In some embodiments, a perhydrolase enzyme comprises one or more substitutions at one or more amino acid positions equivalent to position(s) in the *M. smegmatis* perhydrolase amino acid sequence set forth in SEQ ID NO:1. In some embodiments, the perhydrolase enzyme comprises any one or any combination of substitutions of amino acids selected from M1, K3, R4, I5, L6, C7, D10, S11, L12, T13, W14, W16, G15, V17, P18, V19, D21, G22, A23, P24, T25, E26, R27, F28, A29, P30, D31, V32, R33, W34, T35, G36, L38, Q40, Q41, D45, L42, G43, A44, F46, E47, V48, I49, E50, E51, G52, L53, S54, A55, R56, T57, T58, N59, 160, D61, D62, P63, T64, D65, P66, R67, L68, N69, G70, A71, S72, Y73, S76, C77, L78, A79, T80, L82, P83, L84, D85, L86, V87, N94, D95, T96, K97, Y99F100, R101, R102, P104, L105, D106, I107, A108, L109, G110, M111, S112, V113, L114, V115, T116, Q117, V118, L119, T120, S121, A122, G124, V125, G126, T127, T128, Y129, P146, P148, W149, F150, I153, F154, I194, and F196.

In some embodiments, a perhydrolase enzyme comprises one or more of the following substitutions at one or more amino acid positions equivalent to position(s) in the *M. smegmatis* perhydrolase amino acid sequence set forth in SEQ ID NO:1: L12C, Q, or G; T25S, G, or P; L53H, Q, G, or S; S54V, L A, P, T, or R; A55G or T; R67T, Q, N, G, E, L, or F; K97R; V125S, G, R, A, or P; F154Y; F196G.

In some embodiments, a perhydrolase enzyme comprises a combination of amino acid substitutions at amino acid positions equivalent to amino acid positions in the *M. smegmatis* perhydrolase amino acid sequence set forth in SEQ ID NO:1: L12I S54V; L12M S54T; L12T S54V; L12Q T25S S54V; L53H S54V; S54P V125R; S54V V125G; S54V F196G; S54V K97R V125G; or A55G R67T K97R V125G.

In some embodiments, a perhydrolase enzyme has a perhydrolysis:hydrolysis ratio of at least 1.

Assessment of Biofilm Removal

Biofilm removal may be measured with a crystal violet assay. Samples are immersed in a solution of crystal violet (0.31% w/v) for ten minutes prior to rinsing three times in phosphate buffered saline (PBS) to remove unbound stain. Bound stain retained by a biofilm is extracted with 95% ethanol and the absorbance of the crystal violet/ethanol solution is read at 540 nm. Percent removal of a biofilm is calculated as [(1-Fraction remaining biofilm)×100]. Fraction remaining biofilm is calculated by subtracting the absorbance of the medium+enzyme solutions from the absorbance of the solutions extracted from the enzyme treated biofilms, divided by the difference in absorbance from that of untreated control biofilms minus the absorbance of the growth medium only.

Biofilm removal may also be assessed by suspending cells from a treated biofilm in a buffer such as phosphate buffered saline (PBS), plating cells on a suitable nutrient containing growth medium, and counting the number of cells that grow on the medium. Reduction in viable cell count may be determined by comparison with the number of cells that grow from a suspension prepared from a control untreated biofilm.

Methods

The invention provides methods for removal of biofilms from surfaces. Removal of a biofilm refers to reduction or elimination of the biofilm from a surface. Methods of the invention comprise application of one or more perhydrolase enzyme and a removal enzyme mixture as described above to a biofilm on a surface at an enzyme dosage level and for an amount of time sufficient to reduce the biofilm by at least about 20, 25, 30, 35, 40, 45, 50, 55, 60, 65, 70, 75, 80, 85, 90, 95, 96, 97, 98, or 99 percent. Percent reduction of a biofilm refers to reduction in the number of viable cells in the biofilm in comparison to the number of viable cells and/or total cells in the biofilm prior to treatment. In some embodiments, the biofilm to be treated comprises, consists of, or consists essentially of *Pseudomonas aeruginosa*, *Listeria monocytogenes*, or *Staphylococcus aureus*. Methods of the invention also include prophylactic prevention of formation or growth of a biofilm on a surface.

In some embodiments, the removal enzyme mixture is selected from protease, glucanase and esterase; protease, glucanase, esterase and mannanase; protease, glucanase, phospholipase and mannanase; three proteases, glucanase, phospholipase and mannanase; three proteases, phospholipase, esterase and mannanase; three proteases, glucanase and mannanase; two proteases, cellulase, glucanase, phospholipase and mannanase; protease, glucanase and mannanase; protease, cellulase, phospholipase and esterase; two proteases, glucanase, phospholipase and esterase; two proteases, glucanase, phospholipase and mannanase; three proteases, cellulase, phospholipase and glucanase; three proteases, cellulase, phospholipase and mannanase; three proteases, glucanase, phospholipase and esterase; protease, cellulase, glucanase, phospholipase and esterase; two or more amylases and glucanase; at least three amylases; at least two amylases, glucanase and protease. In some embodiments, one or more commercially available protease selected from PROPERASE, PURAFECT, MULTIFECT NEUTRAL, FNA, and GC106 is included in the removal enzyme mixture. In some embodiments, the commercially available cellulase PURADAX is included in the removal enzyme mixture. In some embodiments, the commercially available esterase CUTINASE is included in the removal enzyme mixture. In some embodiments, a commercially available mannanase selected from GC265 and HEMICELL is included in the removal enzyme mixture. In some embodiments, the commercially available glucanase LAMIINEX BG is included in the removal enzyme mixture. In some embodiments, an endo-arabinase is further included in the removal enzyme mixture.

In some embodiments, the removal enzyme mixture comprises three proteases, glucanase, phospholipase, and mannanase. In one embodiment, the proteases are from *Bacillus subtilis* EC 3.3.2.6 and *Bacillus alcalophilus* EC 3.4.2.6, the glucanase is from *Trichoderma* species EC 3.3.1.6, the phospholipase is from *Streptomyces* species EC 3.1.1.4, and the mannanase is from *Bacillus lentus*. In one embodiment, the removal enzyme mixture comprises or consists of PROPERASE, PURAFECT, FNA, LAMINEX BG, GC265, and LYSOMAX.

In one embodiment, the perhydrolase is the perhydrolase enzyme from *M. smegmatis* (SEQ ID NO:1) or a variant or homolog thereof.

Perhydrolase enzyme(s) and removal enzyme mixture may be applied to a biofilm simultaneously (in contact with the biofilm at the same time) or sequentially (in contact with the biofilm at different times). When applied simultaneously, the perhydrolase enzyme(s) and removal enzyme mixture may be added from a single composition that contains all of the enzymes or from separate perhydrolase containing and removal enzyme mixture containing compositions.

In some embodiments, application of perhydrolase enzyme(s) is sequential, with perhydrolase added first and removal enzyme mixture added afterward. In one embodiment, perhydrolase is applied to the biofilm, removed from the biofilm, and then removal enzyme mixture is applied to the biofilm. In some embodiments, the removal enzyme mixture is added about 15 to about 60 minutes, e.g., about 15, 30, 45, or 60 minutes, after the perhydrolase enzyme is removed.

In one embodiment, the removal enzyme mixture comprises or consists of PROPERASE, PURAFECT, FNA, LAMINEX BG, GC265, and LYSOMAX, and the perhydrolase is the perhydrolase enzyme from *M. smegmatis* (SEQ ID NO:1), the perhydrolase and removal enzyme mixture are added sequentially, and the perhydrolase enzyme is added before the removal enzyme mixture.

In some embodiments, substrates for the perhydrolase enzyme are included in the perhydrolase containing composition that is applied to the biofilm. For example, propylene glycol diacetate (PGD) and percarbonate may be included when the perhydrolase is applied to the biofilm.

The effects of perhydrolase and removal enzyme mixture on a biofilm may be additive (i.e., extent of biofilm removal approximately the sum of removal with perhydrolase alone and removal with enzyme mixture alone) or synergistic (i.e., extent of biofilm removal greater than the sum of removal with perhydrolase alone and removal with enzyme mixture alone).

In some embodiments, the removal enzyme mixture contains about 1% to about 6% total enzyme by weight. In some embodiments, the perhydrolase enzyme is used at a concentration of about 0.01% to about 0.0001% by weight.

Kits

The invention also provides kits. Kits comprise a perhydrolase enzyme and a removal enzyme mixture in amounts sufficient for use in a method for biofilm treatment as described herein. In one embodiment, the perhydrolase enzyme and the removal enzyme mixture are in separate containers. In another embodiment, the perhydrolase enzyme and the removal enzyme mixture are in the same container. The removal enzyme mixture may contain any of the enzyme combinations described above. The perhydrolase enzyme may comprise, consist of, or consist essentially of the amino acid sequence set forth in SEQ ID NO:1, or a variant or homolog thereof, as described above. Enzymes provided in a kit may be supplied in solid or liquid form. The kit may further include buffers, substrates, or other suitable components for enzymatic activity and/or stability. For example, the kit may comprise substrates for perhydrolase activity, for example, propylene glycol diacetate (PGD) and percarbonate. The kit may include instructions for use in a method for biofilm treatment as described herein.

Suitable packaging is provided. As used herein, "packaging" refers to a solid matrix or material customarily used in a system and capable of holding within fixed limits one or more components of a kit as described herein, e.g., enzymes, buffers, substrates. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Instructions may be provided in printed form or in the form of an electronic medium such as a floppy disc, CD, or DVD, or in the form of a website address where such instructions may be obtained.

The following examples are intended to illustrate, but not limit, the invention.

EXAMPLES

Example 1

Screening of Enzyme Mixtures for Removal of *Pseudomonas Aeruginosa* Biofilms

General Experimental Setup

A high-throughput method was used for screening a large number of mixtures of enzymes based on a designed study matrix of enzymes. PBS and acetate buffers were used to prepare the solutions (Tris buffer: pH 7.0 or 8.5 and acetate buffer: pH 5.0). Various enzyme mixture combinations were made according to pH and temperature specifications of the enzymes. A table containing all the 375 different combinations is included as an attached Appendix A. A 96 well method was used to screen the 375 different combinations of enzymes with 4 replicates for each. This analysis allowed for the formation of biofilms in the wells of 96 well microtitre plates, which can be used to provide up to 96 different test samples.

Bacterial inoculum culture (*Pseudomonas aeruginosa*, PO1, biofilm forming) was grown in tryptic soy broth (TSB) at 21° C. overnight in a shake flask. 20 ml of this broth was then added to another 180 ml of fresh tryptic soy broth in another shake flask. 200 ul of this diluted inoculum was then added to each well of a 96 well plate using a 96 pin replicator. Every 8-10 hours, nutrients, planktonic cells and media were aspirated and replaced with fresh TSB medium. The biofilms were grown in the wells for 24 hours at 21° C.

Following biofilm formation, media was removed from the wells of the 96 well plate and the various enzyme and control treatment solutions were transferred to the wells of the plate. The biofilms were allowed to soak for a given period of time (90 minutes was used for this study). The wells were then rinsed twice, with deionized water, to remove any remaining treatment solution and suspended cells from the system. The biofilm was then stained with crystal violet for 10 minutes. The wells were each rinsed 4 times to remove any excess stain from the system, and then eluted with 300 µl of ethanol. The elution step improved the detection of stain during the analyses. The plate was then immediately read with a microtiter plate reader (*J. Microbiological Methods* (2003)

54:269-276). All treatments were run with at least 4 replicates. Under the screening conditions, bleach controls had a 75% reduction at pH 7.0, 75% at pH 5.0, and a 93% at pH 8.

Biofilm Removal Under Acidic pH Conditions

Specific enzymes such as proteases, lipases, cellulases, and other carbohydrases which are catalytically effective for hydrolytic reactions under acidic conditions (pH 5) were screened for their efficacy to remove biofilm. For example, GC106 acidic protease was used for this study in combination with lipases, cellulases and other carbohydrases which are catalytically effective under acidic conditions. 17 enzyme combinations screened from this study reached 69-88% biofilm removal.

Biofilm Removal Under Neutral pH Conditions

Specific enzymes such as proteases, lipases, cellulases, and carbohydrases which are catalytically effective for hydrolytic reactions under neutral conditions (pH 7) were selected to screen for their efficacy to remove biofilm. For example, a neutral protease was used for this study in combinations with lipases, cellulases and other carbohydrases which are catalytically effective under neutral conditions. 5 enzyme combinations screened from this study reached 71-84% biofilm removal.

Biofilm Removal Under Basic pH Conditions

Specific enzymes such as alkaline proteases, lipases, cellulases, and other carbohydrases which are catalytically effective for hydrolytic reactions under alkaline conditions (pH 8.4) were selected to screen for their efficacy to remove biofilm. For example, serine proteases such as FNA, PURAFECT, and PROPERASE were used for this study in combinations with lipases, cellulases and other carbohydrases which are catalytically effective under basic conditions. 11 enzyme combinations screened from this study reached 70-80% biofilm removal.

Statistical Analysis of Data

The data was analyzed for statistical significance. An analysis on the variance determined enzyme mixtures shown below in Table 1 to be statistically different from the controls. The family-wise error rate was set at 0.05; that is, to be 95% confident that there will be no false positive results in one set of 143 test results. Details of this method for statistical analysis can be found at http://core.ecu.edu/psyc/wuenschk/docs30/multcomp.doc and the concept is well illustrated at http://www.brettscaife.net/statistics/introstat/08multiple/lecture.html.

Results

Efficacious enzyme mixtures for biofilm removal of at least 40% biofilm are listed in Table 1 in their order of reduction for each of the different sets of enzymes.

TABLE 1

Biofilm removal for various enzyme combinations.

| Enzyme combination | Percent Removal | Conditions |
|---|---|---|
| Bleach Control | 93 | Basic |
| Pep 3, Cel 2, Pal 2 | 84 | Basic |
| Pep 3, Cel 2, Car 1, Pal 2 | 82 | Basic |
| Pep 3, Cel 2, Car 1, Pal 1 | 80 | Basic |
| Pep 1, 2, 4, Cel 2, Car 1, Pal 1 | 80 | Basic |
| Pep 1, 2, 4, Car 1, Pal 1, Pal 2 | 78 | Basic |
| Pep 1, 2, 4, Cel 2, Car 1 | 77 | Basic |
| Pep 2, 4, Cel 1, Cel 2, Car 1, Pal 1 | 76 | Basic |
| Pep 4, Cel 1, Pal 1, Pal 2 | 75 | Basic |
| Pep 2, 4, Cel 2, Pal 1 | 75 | Basic |
| Pep 1, 4, Cel 2, Car 1, Pal 1 | 74 | Basic |
| Bleach Control | 75 | Neutral |

TABLE 1-continued

Biofilm removal for various enzyme combinations.

| Enzyme combination | Percent Removal | Conditions |
|---|---|---|
| Pep 1, 2, 4, Cel 1 Cel 2, Pal 1 | 72 | Neutral |
| Pep 1, 2, 4, Cel 1, Car 1, Pal 1 | 72 | Neutral |
| Pep 1, 2, 4, Cel 2, Pal 1, Pal 2 | 72 | Neutral |
| Pep 3, Cel 1, Cel 2, Pal 1, Pal 2 | 72 | Neutral |
| Pep 1, 4, Cel 2, Pal 1, Pal 2 | 70 | Neutral |
| Bleach Control | 75 | Acid |
| Car 2 & 7, Cel 2 | 88 | Acid |
| Car 2 & 4, Cel 2 | 83 | Acid |
| Car 2 & 7 | 81 | Acid |
| Car 2 & 7, Pep 5 | 81 | Acid |
| Car 2, Pep 5 | 81 | Acid |
| Car 2 & 6 | 78 | Acid |
| Car 2 & 4, Pep5 | 78 | Acid |
| Car 2 & 7, Cel 2, Pep 5 | 77 | Acid |
| Car 2 & 5, Pep 5 | 77 | Acid |
| Car 2 & 4, Cel 2, Pep 5 | 77 | Acid |
| Car 7, Cel 2 | 75 | Acid |
| Car 2 & 4 | 75 | Acid |
| Car 6, Cel 2 | 74 | Acid |
| Car 2, Cel 2, Pep 5 | 72 | Acid |
| Car 7, Cel 2, Pep 5 | 72 | Acid |
| Car 2 & 6, Cel 2 | 69 | Acid |
| Car 2& 5, Cel 2, Pep 5 | 69 | Acid |

TABLE 2

Key for enzymes in the mixtures shown in Table 1.

| Code | Enzyme Name | Enzyme Type |
|---|---|---|
| CAR1 | GC265 | Mannanase |
| CAR2 | SPEZYME FRED-L | Alpha amylase |
| CAR4 | ARIS SUMIZYME | 1,5-alpha L arabinase |
| CAR5 | ACH SUMIZYME | Beta mannanase |
| CAR6 | BIOCON M1 | Amylase mixture |
| CAR7 | CUCONC SUMIZYME | Amylase mixture |
| CEL1 | PURADAX | Cellulase |
| CEL2 | LAMINEX BG | Glucanase |
| PAL1 | LYSOMAX | Phospholipase |
| PAL2 | CUTINASE | Esterase |
| PEP1 | PROPERASE | Protease |
| PEP2 | PURAFECT | Protease |
| PEP3 | MULTIFECT NEUTRAL | Protease |
| PEP4 | FNA | Protease |
| PEP5 | GC106 | Protease |

Data provided by the high-throughput method was useful for screening a large number of mixtures. Further investigation of the candidate mixtures was next performed to confirm their effectiveness against biofilms, including biofilms of *Pseudomonas aeruginosa, Listeria monocytogenes, Staphylococcus aureus*, and drinking water consortium biofilms, as described in the examples below.

Example 2

Evaluation of Table 1 Enzyme Mixtures in CDC Biofilm Reactor

Experimental Method

Enzyme mixtures in Table 1 were evaluated for biofilm removal using a laboratory model system, the CDC Biofilm Reactor (model CBR 90, Biosurface Technologies Corporation, Bozeman, Mont.). This system was developed by the Centers for Disease Control and has been used to study biofilms formed by various bacterial species. The CDC Biofilm Reactor consists of a one-liter vessel with eight polypropylene coupon holders suspended from the lid. Each coupon holder can accommodate three 0.5-inch diameter sample coupons. For the experiments reported herein, the sample coupons were constructed from polystyrene, to be consistent with high-throughput screening assays that were performed using polystyrene microtiter plates. Two CDC biofilm reactors were operated in parallel providing a total of 48 sample coupons per experiment. Liquid growth medium entered through the top of the vessel and exited via a side-arm discharge port. A magnetic stir bar incorporating a mixing blade provided fluid mixing and surface shear.

*Pseudomonas aeruginosa* Biofilm

CDC Biofilm Reactor vessels with a working volume of approximately 400 ml containing 10%-strength tryptic soy broth medium were inoculated with *P. aeruginosa* and operated in batch mode (no inflowing medium) for 6 hours at 37° C. After establishing the batch culture, flow of medium at a rate of 600 ml/hr was provided for an additional 42 hours to establish *P. aeruginosa* biofilms on the polystyrene sample coupons. At the end of the biofilm growth period, six control coupons were removed from each of the two reactors and rinsed with sterile phosphate-buffered saline (PBS) to remove unattached bacteria. Three of the coupons from each reactor were then analyzed for biofilm using the crystal violet staining method described below. The remaining three control coupons from each reactor were sonicated in PBS, serially diluted, and plated on tryptic soy agar to enumerate the number of culturable bacteria within the biofilm.

The remaining 30 test coupons and 6 control coupons were transferred to 12-well tissue culture plates and treated with the selected high performing enzyme mixtures, used at an enzyme dosage of 1% wt total enzyme, in buffer for 90 minutes at 45° C. The six control coupons were treated with the same buffer used to prepare the enzyme mixtures. Following the treatments, the coupons were rinsed three times with PBS and analyzed for biofilm using the crystal violet staining method. This method consisted of immersing the coupons in a solution of crystal violet (0.31% w/v) for ten minutes, rinsing the coupons three times in PBS to remove unbound stain. The bound stain was then extracted from the biofilm using 95% ethanol and the absorbance of the crystal violet/ethanol solution was read at 540 nm. Percent removal of *Pseudomonas* biofilm was calculated from [(1-Fraction remaining biofilm)×100]. Fraction remaining biofilm was calculated by subtracting the absorbance of the medium+ enzyme solutions from the absorbance of the solutions extracted from the enzyme treated biofilms and that was divided by the difference in absorbance between the untreated control biofilms and the absorbance of the growth medium only. The average thickness of the biofilms was 0.2 mm.

Biofilm percent removal assessed using biofilms grown in the CDC-BR were some what lower than those determined previously using the High-Throughput Screening Assay (HTA), as shown below in Table 3. This is likely due to the more tenacious nature of biofilms grown in the CDC-BR. The CDC-BR creates a higher shear environment than the 96-well microtiter plate method used for the HTA, which likely resulted in biofilms that were more difficult to remove. Nonetheless, biofilm removal of up to 77% was observed with some of the enzyme combinations. The combination of "Pep 1,2,4, Cel 2, Car1, Pal 1" ranked ninth in the HTA tests at 80% removal but performed better than any other combination on CDC-BR biofilms with 77% removal. The highest percent biofilm removal was observed for enzyme mixtures prepared in alkaline buffer (50 mM Bis-Tris, pH 8.5).

TABLE 3

Results of biofilm removal tests using *Pseudomonas aeruginosa* biofilms grown in the CDC Biofilm Reactor

| Enzyme combination | HTA % Removal* | CDC-BR % Removal | CDC-BR St. Dev. | CDC-BR n |
|---|---|---|---|---|
| Bleach Control | 75-93 | 75-93 | | |
| Pep 3, Cel 2, Pal 2 | 84 | 51 | 15 | 4 |
| Pep 3, Cel 2, Car 1, Pal 2 | 82 | 61 | 19 | 4 |
| Pep 3, Cel 2, Car 1, Pal 1 | 80 | 51 | 17 | 4 |
| Pep 1, 2, 4, Cel 2, Car 1, Pal 1 | 80 | 77 | 5 | 3 |
| Pep 1, 2, 4, Car 1, Pal 1, Pal 2 | 78 | 73 | 13 | 3 |
| Pep 1, 2, 4, Cel 2, Car 1 | 77 | 75 | 7 | 3 |
| Pep 2, 4, Cel 1, Cel 2, Car 1, Pal 1 | 76 | 58 | 13 | 3 |
| Pep 3, Cel 2, Car 1 | 76 | 51 | 26 | 3 |
| Pep 4, Cel 1, Pal 1, Pal 2 | 75 | 66 | 4 | 3 |
| Pep 2, 4, Cel 2, Pal 1 | 75 | 63 | 8 | 3 |
| Pep 1, 4, Cel 2, Car 1, Pal 1 | 74 | 59 | 23 | 3 |
| Pep 1, 2, 4, Cel 1, Car 1, Pal 1 | 72 | 74 | 9 | 3 |
| Pep 1, 2, 4, Cel 2, Pal 1, Pal 2 | 72 | 58 | 28 | 3 |
| Pep 3, Cel 1, Cel 2, Pal 1, Pal 2 | 71 | 60 | 9 | 4 |
| Car 2&4, Cel 2 | 83 | 67 | 5 | 3 |
| Car 2&7 | 81 | 51 | 11 | 2 |
| Car 2&7, Pep 5 | 81 | 37 | 25 | 3 |
| Car 2, Pep 5 | 81 | 35 | 32 | 2 |
| Car 2&6 | 78 | 15 | 20 | 2 |
| Car 2&4, Pep5 | 78 | 28 | 4 | 2 |
| Car 2&7, Cel 2, Pep 5 | 77 | 35 | n/a | 1 |
| Car 2&5, Pep 5 | 77 | 31 | n/a | 1 |
| Car 2&4, Cel 2, Pep 5 | 77 | 24 | n/a | 1 |
| Car 7, Cel 2 | 75 | 36 | 33 | 3 |
| Car 2&4 | 75 | 50 | 12 | 3 |
| Car 6, Cel 2 | 74 | 26 | 4 | 2 |
| Car 2, Cel 2, Pep 5 | 72 | 9 | 7 | 2 |
| Car 7, Cel 2, Pep 5 | 72 | 54 | 18 | 3 |

Testing of 30 enzyme mixtures using the CDC Biofilm Reactor system with *Pseudomonas aeruginosa* revealed twenty enzyme mixtures with biofilm removal greater than 40%, 19 mixtures with biofilm removal percentages greater than 50%, 10 mixtures with biofilm removal percentages greater than 60% and 4 mixtures above 70%. Most of the enzyme mixtures found to be most effective for *Pseudomonas* biofilm removal are in alkaline to neutral conditions based on both HTP and CDC Reactor based biofilm removal analysis of *Pseudomonas aeruginosa* biofilm. Under acidic conditions, the highest performing mixture found was Car2+Car7+ Cel2. Cel2 was found in most of the efficacious enzyme mixtures tested for *Pseudomonas* biofilm removal.

Example 3

The enzyme mixtures listed below were tested to assess efficacy against three other major commercially relevant biofilms, based upon the CDC Biofilm Reactor data on *Pseudomonas* and a separate HTP study on a dental biofilm, four species model. In view of practical considerations with regard to time available for cleaning and economy of dosage, the cleaning enzyme mixture contact time with biofilm coupons was reduced to 40 minutes and final combined enzyme concentration of all the enzyme components in the enzyme mixtures was limited to a total of 1%. For example, the PEP5+CAR2+CEL3 enzyme mix contained 0.33+0.33+ 0.34% of each enzyme making the final enzyme mixture dosage for testing at 1%.

Testing was conducted at the three pHs listed below, using six enzyme mixtures listed below. The tests were conducted on *Listeria, Staphylococcus*, and drinking water biofilms. The results are provided in Examples 4 through 6.

pH 5.5

1. PEP5+CAR2+CEL3
2. PEP5+CAR2+CEL2 pH 7.0

3. PEP6+PAL2+CEL3
4. PEP3+PAL2+CEL2 pH 8.5

5. PEP1+PEP2+PEP4+CEL2+CAR1+PAL1
6. PEP4+CEL1+PAL1+PAL2

The most effective enzyme mixture for all types of biofilm removal was a combination of FNA, Purafect L, Properase L, Laminex BG, GC265, and Lysomax under mild alkaline conditions. For neutral to acidic pH conditions, the most effective enzyme mixture included Multifect Neutral, Laminex BG, and Cutinase enzymes.

Example 4

*Listeria monocytogenes* Biofilm

CDC Biofilm Reactor vessels having stainless steel coupons with a working volume of approximately 400 ml containing 10%-strength Brain Heart Infusion (BHI) medium were inoculated with 4 ml of an overnight culture of *Listeria monocytogenes* (ATCC 19112) in 10% BHI at 37° C. The reactor was operated in a batch mode for 24 hours followed by the continuous feed of flowing BHI medium at 7 ml/min for the next 24 hours. After 48 hours (24 batch+24 continuous), the reactor was stopped and dismantled.

Sterile tweezers were used to remove all the stainless steel coupons from the wands, touching the front and back of the coupons as little as possible, and the coupons were placed in sterile 12 well plates for treatment.

A total of 24 coupons per reactor were available and three coupons each were treated with each enzyme mixture combination (six combinations, total 1% enzyme mix concentration of all the enzyme components combined, 40 minutes, 45° C.). Three coupons were not treated and were used as untreated controls. All of the treated coupons were removed from treatment, rinsed in PBS three times, and placed in 75% crystal violet solution in a twelve well plate, for ten minutes. After staining, the coupons were rinsed in PBS three times and placed in 5.0 ml 95% ethanol and placed on the shaker at room temperature for 5 minutes to elute the crystal violet. The eluted solutions were then pipetted into cuvettes and read on the spectrophotometer at 540 nm. Percent removal of *Listeria* biofilm was calculated from [(1-Fraction remaining biofilm)×100]. Fraction remaining biofilm was calculated by subtracting the absorbance of the medium+enzyme solutions from the absorbance of the solutions extracted from the enzyme treated biofilms and that was divided by the difference in absorbance between the untreated control biofilms and the absorbance of the growth medium only.

TABLE 4

Removal of *Listeria* biofilms by enzyme mixtures in CDC reactor

| Enzyme combination | CDC-BR % Removal | CDC-BR St. Dev. | CDC-BR n |
|---|---|---|---|
| Bleach Control (Basic) | 93 | | |
| Bleach Control (Neutral) | 75 | | |
| Bleach Control (Acid) | 75 | | |
| PEP5 + CAR2 + CEL3 | 39 | 8 | 3 |
| PEP5 + CAR2 + CEL2 | 30 | 35 | 3 |
| PEP3 + PAL2 + CEL2 | 40 | 2 | 3 |
| PEP6 + PAL2 + CEL3 | 41 | 10 | 3 |
| PEP4 + CEL1 + PAL1 + PAL2 | 51 | 21 | 3 |
| PEP1 + PEP2 + PEP4 + CEL2 + CAR1 + PAL1 | 56 | 13 | 3 |

Example 5

*Staphylococcus aureus* Biofilm

CDC Biofilm Reactor vessels having polyurethane coupons with a working volume of approximately 400 ml containing 10% Tryptic soy broth medium (TSB) were inoculated with 4 ml of an overnight culture of *Staphylococcus aureus* (SRWC-10943) in 10% TSB medium at 37° C. The CDC reactor was operated in a batch mode for 24 hours followed by the continuous feed of flowing TSB medium at 7 ml/min for the next 24 hours. After 48 hours (24 batch+24 continuous), the reactor was stopped and dismantled.

Sterile tweezers were used to remove all the polyurethane coupons from the wands, touching the front and back of the coupons as little as possible, and the coupons were placed in sterile 12 well plates for treatment.

A total of 24 coupons per reactor were available and three coupons each were treated with each enzyme mixture combination (seven combinations, a total of 1% enzyme mix concentration of all the components combined, 40 minutes, 45° C.). Three coupons were not treated and were used as untreated controls. All of the treated coupons were removed from treatment, rinsed in PBS three times, and placed in 75% crystal violet solution in a twelve well plate, for ten minutes. After staining, the coupons were rinsed in PBS three times and placed in 5.0 ml 95% ethanol and placed on the shaker at room temperature for 5 minutes to elute the crystal violet. The eluted solutions were then pipetted into cuvettes and read on the spectrophotometer at 540 nm. Percent removal of *Listeria* biofilm was calculated from [(1-Fraction remaining biofilm)×100]. Fraction remaining biofilm was calculated by subtracting the absorbance of the medium+enzyme solutions from the absorbance of the solutions extracted from the enzyme treated biofilms and that was divided by the difference in absorbance between the untreated control biofilms and the absorbance of the growth medium only.

TABLE 5

Removal of *Staphylococcus aureus* biofilms by enzyme mixtures in CDC Reactor

| Enzyme combination | CDC-BR % Removal | CDC-BR St. Dev. | CDC-BR n |
|---|---|---|---|
| Bleach control (Basic, Neutral, Acid) | 93, 75, 75 | | |
| PEP5 + CAR2 + CEL3 | 25 | 8 | 3 |
| PEP5 + CAR2 + CEL2 | 30 | 10 | 3 |
| PEP3 + PAL2 + CEL2 | 36 | 8 | 3 |

TABLE 5-continued

Removal of *Staphylococcus aureus* biofilms
by enzyme mixtures in CDC Reactor

| Enzyme combination | CDC-BR % Removal | CDC-BR St. Dev. | CDC-BR n |
|---|---|---|---|
| PEP6 + PAL2 + CEL3 | 32 | 19 | 3 |
| PEP4 + CEL1 + PAL1 + PAL2 | 28 | 18 | 3 |
| PEP1 + PEP2 + PEP4 + CEL2 + CAR1 + PAL1 | 41 | 8 | 3 |

TABLE 6

Removal of drinking water consortia biofilms
by enzyme mixtures in CDC Reactor

| Enzyme combination | CDC-BR % Removal | CDC-BR St. Dev. | CDC-BR n |
|---|---|---|---|
| Bleach control (Basic, Neutral, Acid) | 93, 75, 75 | | |
| PEP5 + CAR2 + CEL3 | 7 | 29 | 4 |
| PEP5 + CAR2 + CEL2 | 12 | 18 | 4 |
| PEP3 + PAL2 + CEL2 | 47 | 22 | 4 |
| PEP6 + PAL2 + CEL3 | 43 | 16 | 4 |
| PEP4 + CEL1 + PAL1 + PAL2 | 53 | 8 | 4 |
| PEP1 + PEP2 + PEP4 + CEL2 + CAR1 + PAL1 | 59 | 8 | 4 |

Example 6

Drinking Water Consortium Biofilm

A 20 L sterile carboy with 19 L of BAC/GAC drinking water (containing low CFU mixed drinking water consortium) and 1 L of carbon amendment solution was prepared with the following ingredients to achieve the additional carbon concentration:

L-glutamic acid . . . 0.0047 g/L
L-aspartic acid . . . 0.0053 g/L
L-serine . . . 0.0055 g/L
L-alanine . . . 0.0047 g/L
D+ glucose . . . 0.0048 g/L
D+ galactose . . . 0.0048 g/sL
D-arabinose . . . 0.0048 g/L Sterile CDC reactors were placed in a laminar flow hood and were filled to the outlet with BAC/GAC water. In the 37° C. incubator, connection of all the tubing to the inlet and outlet was made and CDC reactors were placed on the stir plate. The reactors were run for 24 hours in batch followed by the continuous flow of carbon supplemented BAC/GAC water at 7 ml/min for the next 24 hours. At the end of 48 hours (24 batch+24 continuous), the influx flow was turned off, the media was poured out from the reactors into a waste container, and the reactors were placed in a laminar flow hood.

Using sterile tweezers all the coupons were removed from the wands. PVC coupons containing drinking water consortia biofilm were then placed in sterile 12 well plates for treatment.

A total of 24 coupons per reactor were available and three coupons each were treated with each enzyme mixture combination (seven combinations, a total of 1% concentration, 40 minutes, 45° C.). Three coupons were not treated and were used as untreated controls. All of the treated coupons were removed from treatment, rinsed in PBS three times and placed in 75% crystal violet solution in a twelve well plate, for ten minutes. After staining, the coupons were rinsed in PBS three times and placed in 5.0 ml 95% ethanol and placed on the shaker at room temperature for 5 minutes to elute the crystal violet. The eluted solutions were then pipetted into cuvettes and read on the spectrophotometer at 540 nm. Percent removal of *Listeria* biofilm was calculated from [(1−Fraction remaining biofilm)×100]. Fraction remaining biofilm was calculated by subtracting the absorbance of the medium+enzyme solutions from the absorbance of the solutions extracted from the enzyme treated biofilms and that was divided by the difference in absorbance between untreated control biofilms and the absorbance of the growth medium only.

Example 7

Removal of Biofilms with Enzyme Mixtures and Perhydrolase Enzyme

Methods

CDC biofilm reactors (http://www.imt.net/~mitbst/CD-Creactor.html) were aseptically filled with an appropriate medium plus 4.0 ml of one of the following innocula:

Overnight culture of *Pseudomonas aeruginosa* in 10% Tryptic Soy Broth (TSB). Coupons for this series were polystyrene.

Overnight culture of *Listeria monocytogenes* (ATCC 19112) in 10% Brain Heart Infusion (BHI). Coupons for this series were stainless steel.

Drinking water consortia in water with carbon amendment. Coupons for this series were polyvinyl chloride (PVC).

For *Pseudomonas* and *Listeria* cultures, reactors were incubated at 37° C. for 24 hours in batch mode. At T=24 hr, continuous flow was initiated at 7 ml/min for the next 24 hours. Testing was performed on coupons at T=48 hr (24 hr batch+24 hr continuous).

The drinking water biofilm was brown at room temperature on the benchtop in batch mode for 48 hours, followed by continuous flow for 24 hours. Drinking water coupons were tested at T=72 hr (48 hr batch+24 hr continuous).

Enzyme Treatment

Coupons were placed in sterile 12 well plates for enzyme treatment. The following treatments were performed:

perhydrolase enzyme followed by mixture of PEP1, PEP2, PEP4, CEL2, CAR1, and PAL1 ("removal enzyme mixture")

removal enzyme mixture followed by perhydrolase enzyme perhydrolase enzyme alone Six coupons each were treated with one of the enzyme treatments above or with sterile phosphate buffered saline (PBS) as a control. The treatment time was 90 minutes (45 minutes removal enzyme mixture and 45 minutes perhydrolase enzyme), at 45° C., or 45 minutes at 45° C. when perhydrolase enzyme was used alone. At the end of the treatment time, coupons were removed from treatment solution and rinsed in PBS three times.

Removal enzyme solution: PEP1, PEP2, PEP4, CEL2, CAR1, and PAL1 at a final enzyme concentration for each enzyme of 1% in 50 mM Tris, pH 8.5.

Perhydrolase enzyme solution, final concentration: 100 mM propylene glycol diacetate (PGD), 100 mM percarbonate, 4 ppm S54V variant of SEQ ID NO:1, 400 Mm $KH_2PO_4$, pH 7.1.

Stock solutions for perhydrolase: 125 mM PGD—2 ml/100 ml 400 mM $KH_2PO_4$ (800 µl per 1 ml reaction mixture); 10.5 mg/ml percarbonate (10.5 mg per 1 ml reaction mixture); 20 ppm perhydrolase (200 µl per 1 ml reaction mixture).

Perhydrolase treatment procedure: Percarbonate was weighed out and mixed with $PGD/KH_2PO_4$ buffer to dissolve. (Alternatively, another suitable buffer may be used at pH 6-12, or no buffer added, with percarbonate serving as a buffer.) Perhydrolase was added and the solution was mixed again. The solution was allowed to sit for 20 minutes at room temperature, then used immediately.

Peracetic acid assay solution: 50 ml 125 mM NaCitrate buffer, pH 5.0, 500 µl 100 mM 2,2'-Azino-bis(3-ethylbenzothiazoline-6-sulfonic acid) Diammonium salt, CAS#30931-67-0 (ABTS) in water, 100 µl 25 mM KI in water.

Peracetic acid assay procedure: 25 µl perhydrolase enzyme solution was mixed with 225 µl water. This solution was diluted a second time (25 µl+225 µl water). 25 µl of the final solution was mixed with 75 µl water and subsequently added to 900 µl peracetic acid assay solution in a cuvette. The solution was incubated at room temperature for 3 minutes. Absorbance was read at 420 nm. Peracetic acid concentration was calculated as: $A_{420} \times 0.242$ = [Peracetic Acid] mM.

For the first *P. aeruginosa* PA01 run, the testing scheme was as follows:

| Treatment | Crystal Violet (Biofilm) | Plate Count (Log Reduction) | Coupon total |
|---|---|---|---|
| PBS Control | 3 coupons | 3 coupons | 6 |
| Perhydrolase enzyme, followed by removal enzyme mixture | 3 coupons | 3 coupons | 6 |
| Removal enzymes, followed by perhydrolase enzyme | 3 coupons | 3 coupons | 6 |
| Perhydrolase enzyme alone | 3 coupons | 3 coupons | 6 |
| | | Total | 24 |

Subsequent tests included a treatment with removal enzyme mixture alone, according to the following testing scheme:

| Treatment | Crystal Violet (Biofilm) | Plate Count (Log Reduction) | Coupon total |
|---|---|---|---|
| PBS Control | 2 coupons | 2 coupons | 4 |
| Perhydrolase enzyme, followed by removal enzyme mixture | 3 coupons | 3 coupons | 6 |
| Removal enzymes, followed by perhydrolase enzyme | 3 coupons | 3 coupons | 6 |
| Perhydrolase enzyme alone | 2 coupons | 2 coupons | 4 |
| Removal enzyme mixture alone | 2 coupons | 2 coupons | 4 |
| | | Total | 24 |

Crystal Violet Assay to Determine Removal Efficacy

Coupons from each treatment were placed into a 75% crystal violet solution in a twelve well plate, for ten minutes. After staining, the coupons were rinsed in PBS three times, then placed into 5.0 ml 95% ethanol, and placed on a shaker at room temperature for 5 minutes to elute the crystal violet. The eluted solutions were then pipetted into cuvettes and absorbance read in a spectrophotometer at 540 nm.

Plate Counts to Determine Log Reduction

Coupons from each treatment were placed into sterile conical vials containing 10 ml sterile PBS. The vials were vortexed for 1 minute, sonicated for 2 minutes, and vortexed for 30 seconds, per standardized procedures established in the Medical Biofilm Laboratory, Center for Biofilm Engineering at Montana State University, Bozeman, Mont. (MBL). The bacterial suspensions were serially diluted and plated to determine viable cell counts and log reduction as a result of treatment. For viable counts, *P. aeruginosa* was plated on 100% tryptic soy agar (TSA), *L. monocytogenes* was plated on 1005 BHI agar, and the drinking water consortia was plated on 100% R2A agar.

Results

TABLE 7

Removal of *Pseudomonas aeruginosa* biofilms by enzyme mixtures and perhydrolase enzyme in CDC reactor

| Enzyme combination | Average % Biofilm Reduction (crystal violet)* | Std. Deviation | Average Log Reduction (plate count) | Std. Deviation |
|---|---|---|---|---|
| Perhydrolase, followed by removal enzymes | 30.60 | 5.90 | 2.9 | 0.18 |
| Removal enzymes, followed by perhydrolase | 9.26 | 6.06 | 1.7 | 0.50 |
| Perhydrolase alone | 29.04 | 4.90 | 3.2 | 0.39 |
| Removal enzymes alone | 25.58 | 6.36 | not calculated | not calculated |

*Average of three runs for first three treatments listed in table, and average of two runs for fourth treatment (removal enzymes alone).

TABLE 8

Removal of *Listeria monocytogenes* biofilms by enzyme mixtures and perhydrolase enzyme in CDC reactor

| Enzyme combination | Average % Biofilm Reduction (crystal violet)* | Std. Deviation | Average Log Reduction (plate count) | Std. Deviation |
|---|---|---|---|---|
| Perhydrolase, followed by removal enzymes | 33.24 | not calculated | 1.8 | not calculated |
| Removal enzymes, followed by perhydrolase | 25.30 | not calculated | 0.9 | not calculated |
| Perhydrolase alone | 23.80 | not calculated | 1.9 | not calculated |
| Removal enzymes alone | 23.18 | not calculated | not calculated | not calculated |

*Average of 2 runs for all treatments listed in table.

TABLE 9

Removal of drinking water consortia biofilms by enzyme mixtures and perhydrolase enzyme in CDC reactor

| Enzyme combination | % Biofilm Reduction (crystal violet)* | Log Reduction (plate count) |
|---|---|---|
| Perhydrolase, followed by removal enzymes | 28.4 | 2.0 |
| Removal enzymes, followed by perhydrolase | 28.5 | 1.0 |
| Perhydrolase alone | 29.9 | 2.0 |
| Removal enzymes alone | 21.7 | 1.4 |

*Data based on one run.

Example 8

Removal of *Pseudomonas aeruginosa* Biofilms with Enzyme Mixtures and Perhydrolase Enzyme with and without Substrates Methods A CDC biofilm reactor fitted with 24 polystyrene coupons was filled with approximately 450 ml of 10% TSB plus 4 ml of a 24 hour culture of *Pseudomonas aeruginosa*. The reactor was incubated for 24 hours in batch mode with continuous stirring. At T=24 hr, continuous flow was initiated at 7 ml/min for the next 24 hours. Coupons were placed in sterile 12 well plates at T=48 hr (24 hr batch+24 hr continuous) for enzyme treatment.

Enzyme Treatment

Six coupons each were treated with:
perhydrolase enzyme (S54V variant of SEQ ID NO:1; 4 ppm) without substrates+removal enzyme mixture (1% each enzyme)
perhydrolase enzyme (4 ppm) without substrates
perhydrolase enzyme (4 ppm) with substrates
PBS, 7.2 (control)

Treatment time was 90 minutes total, at a temperature of 45° C. At the end of treatment, coupons were rinsed in PBS three times.

Enzyme Mixtures and Mixing Protocols

Perhydrolase enzyme without substrates+removal enzyme mixture: PEP1, PEP2, CEL2, CAR1, and PAL1 at a total final enzyme concentration for each enzyme of 1% in 400 mM $KH_2PO_4$ buffer at pH 7.1 plus 4 ppm final concentration perhydrolase enzyme.

Perhydrolase enzyme without substrates: 400 mM $KH_2PO_4$ buffer, 4 ppm perhydrolase enzyme.

Perhydrolase enzyme with substrates: 100 mM PGD, 100 mM percarbonate, 4 ppm perhydrolase enzyme, 400 mM $KH_2PO_4$ buffer, pH 7.1. Percarbonate was weighed out and mixed with PGD/$KH_2PO_4$ buffer to dissolve. Perhydrolase was added and the solution was mixed again. The solution was allowed to sit for 20 minutes at room temperature, then used immediately.

PBS: NaCl 8 g/l, KCl 0.2 g/L, $Na_2HPO_4$ 1.15 g/L, and $KH_2PO_4$ 0.2 g/L were mixed. The pH was adjusted to 7.2 and the solution autoclaved.

Testing Scheme

The testing scheme was as follows:

| Treatment | Crystal Violet (Biofilm) | Plate Count (Log Reduction) | Coupon total |
|---|---|---|---|
| PBS Control | 3 coupons | 3 coupons | 6 |
| Perhydrolase enzyme without substrates, plus removal enzyme mixture | 3 coupons | 3 coupons | 6 |
| Perhydrolase enzyme without substrates | 3 coupons | 3 coupons | 6 |
| Perhydrolase enzyme with substrates | 3 coupons | 3 coupons | 6 |
| Total | | | 24 |

Crystal Violet Assay to Determine Removal Efficacy

Coupons from each treatment were placed into a 75% crystal violet solution in a twelve well plate, for ten minutes. After staining, the coupons were rinsed in PBS three times, then placed into 5.0 ml 95% ethanol, and placed on a shaker at room temperature for 5 minutes to elute the crystal violet. The eluted solutions were then pipetted into cuvettes and absorbance read in a spectrophotometer at 540 nm.

Plate Counts to Determine Log Reduction

Three coupons from each treatment were placed into sterile conical vials containing 10 ml sterile PBS. The vials were vortexed for 1 minute, sonicated for 2 minutes, and vortexed for 30 seconds, per standardized procedures established in the MBL. The bacterial suspensions were serially diluted and plated on 100% TSA to determine viable cell counts and log reduction as a result of treatment.

Results

TABLE 10

Removal of *P. aeruginosa* biofilms with enzyme mixtures and perhydrolase enzyme with or without substrates

|  | Absorbance (crystal violet) | % Biofilm reduction | Log cfu/cm² (plate count) | Log reduction |
|---|---|---|---|---|
| Run 1 |  |  |  |  |
| PBS control | 0.746 |  | 8.0 |  |
| Perhydrolase minus substrates | 0.637 | 14.5 | 6.7 | 1.3 |
| Perhydrolase plus substrates | 0.588 | 21.1 | 5.0 | 3.1 |
| Perhydrolase plus substrates, with removal enzymes | 0.504 | 32.4 | 3.7 | 4.4 |
| Run 2 |  |  |  |  |
| PBS control | 0.708 |  | 7.1 |  |
| Perhydrolase minus substrates | 0.582 | 17.8 | 5.6 | 1.6 |
| Perhydrolase plus substrates | 0.464 | 34.4 | 3.8 | 3.4 |
| Perhydrolase plus substrates, with removal enzymes | 0.483 | 31.8 | 3.9 | 3.2 |
| Run 3 |  |  |  |  |
| PBS control | 0.783 |  | 8.4 |  |
| Perhydrolase minus substrates | 0.492 | 37.1 | 6.0 | 2.4 |
| Perhydrolase plus substrates | 0.382 | 51.2 | 4.2 | 4.2 |
| Perhydrolase plus substrates, with removal enzymes | 0.220 | 71.8 | 2.5 | 5.8 |

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

---

We claim:

1. A method for removing biofilm from a surface, said method comprising applying a perhydrolase enzyme and a removal enzyme mixture simultaneously to said biofilm for a time sufficient to reduce said biofilm by at least 25%, wherein the enzymes of said removal enzyme mixture consists of three proteases, a glucanase, a mannanase and an esterase.

2. A method according to claim 1, wherein perhydrolase enzyme and the removal enzyme mixture act synergistically to remove the biofilm from the surface.

3. A method according to claim 1, wherein the biofilm comprises *Pseudomonas aeruginosa*, *Listeria monocytogenes*, or *Staphylococcus aureus*.

4. A method according to claim 1, wherein the proteases of the removal enzyme mixture is a protease from *B. alcalophilus*, a protease from *B. subtilis*, a subtilisin protease, a phospholipase from *S. violceoruber*, a glucanase from Triocderma and a mannanase from *B. lentus*.

5. A method according to claim 1, wherein the perhydrolase enzyme comprises the amino acid sequence set forth in SEQ ID NO:1.

* * * * *

UNITED STATES PATENT AND TRADEMARK OFFICE
CERTIFICATE OF CORRECTION

PATENT NO. : 8,597,927 B2  Page 1 of 1
APPLICATION NO. : 12/810004
DATED : December 3, 2013
INVENTOR(S) : Barnett et al.

It is certified that error appears in the above-identified patent and that said Letters Patent is hereby corrected as shown below:

In the Claims:

In claim 4, column 30, line 42, delete the word "Triocderma" and insert -- Trichoderma --.

Signed and Sealed this
Fourteenth Day of October, 2014

Michelle K. Lee
*Deputy Director of the United States Patent and Trademark Office*